(12) United States Patent
Shakespeare et al.

(10) Patent No.: US 8,184,294 B2
(45) Date of Patent: May 22, 2012

(54) APPARATUS AND METHOD FOR MEASURING HAZE OF SHEET MATERIALS OR OTHER MATERIALS

(75) Inventors: Tarja T. Shakespeare, Savo (FI); John F. Shakespeare, Savo (FI)

(73) Assignee: Honeywell International Inc., Morristown, NJ (US)

( * ) Notice: Subject to any disclaimer, the term of this patent is extended or adjusted under 35 U.S.C. 154(b) by 707 days.

(21) Appl. No.: 12/400,641

(22) Filed: Mar. 9, 2009

(65) Prior Publication Data

US 2010/0226524 A1    Sep. 9, 2010

(51) Int. Cl.
   *G01N 21/00* (2006.01)
(52) U.S. Cl. .................. 356/432; 382/141
(58) Field of Classification Search ............. 356/432
   See application file for complete search history.

(56) References Cited

U.S. PATENT DOCUMENTS

| | | | | |
|---|---|---|---|---|
| 4,623,258 A * | 11/1986 | Task et al. | | 356/432 |
| 5,086,477 A * | 2/1992 | Yu et al. | | 382/145 |
| 5,712,709 A * | 1/1998 | Task et al. | | 356/432 |
| 5,880,476 A * | 3/1999 | Suzuki | | 250/484.4 |
| 6,194,701 B1 | 2/2001 | Task et al. | | |
| 6,618,076 B1 * | 9/2003 | Sukthankar et al. | | 348/180 |
| 7,405,828 B2 * | 7/2008 | Tan et al. | | 356/446 |
| 2004/0008412 A1 * | 1/2004 | Jiang et al. | | 359/487 |
| 2005/0163394 A1 * | 7/2005 | Scholze et al. | | 382/260 |
| 2007/0139735 A1 | 6/2007 | Shakespeare et al. | | |
| 2007/0153278 A1 | 7/2007 | Shakespeare et al. | | |
| 2008/0157013 A1 | 7/2008 | Shakespeare | | |
| 2009/0185185 A1 * | 7/2009 | Shakespeare et al. | | 356/406 |
| 2010/0026987 A1 * | 2/2010 | Maruo et al. | | 356/51 |
| 2011/0194113 A1 * | 8/2011 | Sakai et al. | | 356/432 |

FOREIGN PATENT DOCUMENTS

| | | |
|---|---|---|
| JP | 2000-206030 | 7/2000 |
| JP | 2002-310902 | 10/2002 |

OTHER PUBLICATIONS

Notification of Transmittal of the International Search Report and the Written Opinion of the International Searching Authority, or the Declaration dated Oct. 19, 2010 in connection with International Patent Application No. PCT/US2010/025877.
"Standard Test Method for Haze and Luminous Transmittance of Transparent Plastics", American Society for Testing and Materials, pp. 1-6, 2008.
"Haze", Applications Note, HunterLab, 2008, vol. 9, No. 6, pp. 1-4.

* cited by examiner

*Primary Examiner* — Sath V Perungavoor

(57) ABSTRACT

A method includes illuminating a material with first light and capturing an image of second light transmitted through the material. The method also includes analyzing multiple regions of the image and determining one or more haze measurements associated with the material based on the analyzing. The method further includes storing and/or outputting the one or more haze measurements. Analyzing the multiple regions of the image may include summing pixel values in each region to produce a total pixel value for that region. The multiple regions of the image may include (i) a first region forming a first disc, (ii) a second region forming either a first annular region around the first region or a second disc larger than and including the first disc, and (iii) a third region forming either a second annular region around the second region or a third disc larger than and including the first and second discs.

21 Claims, 4 Drawing Sheets

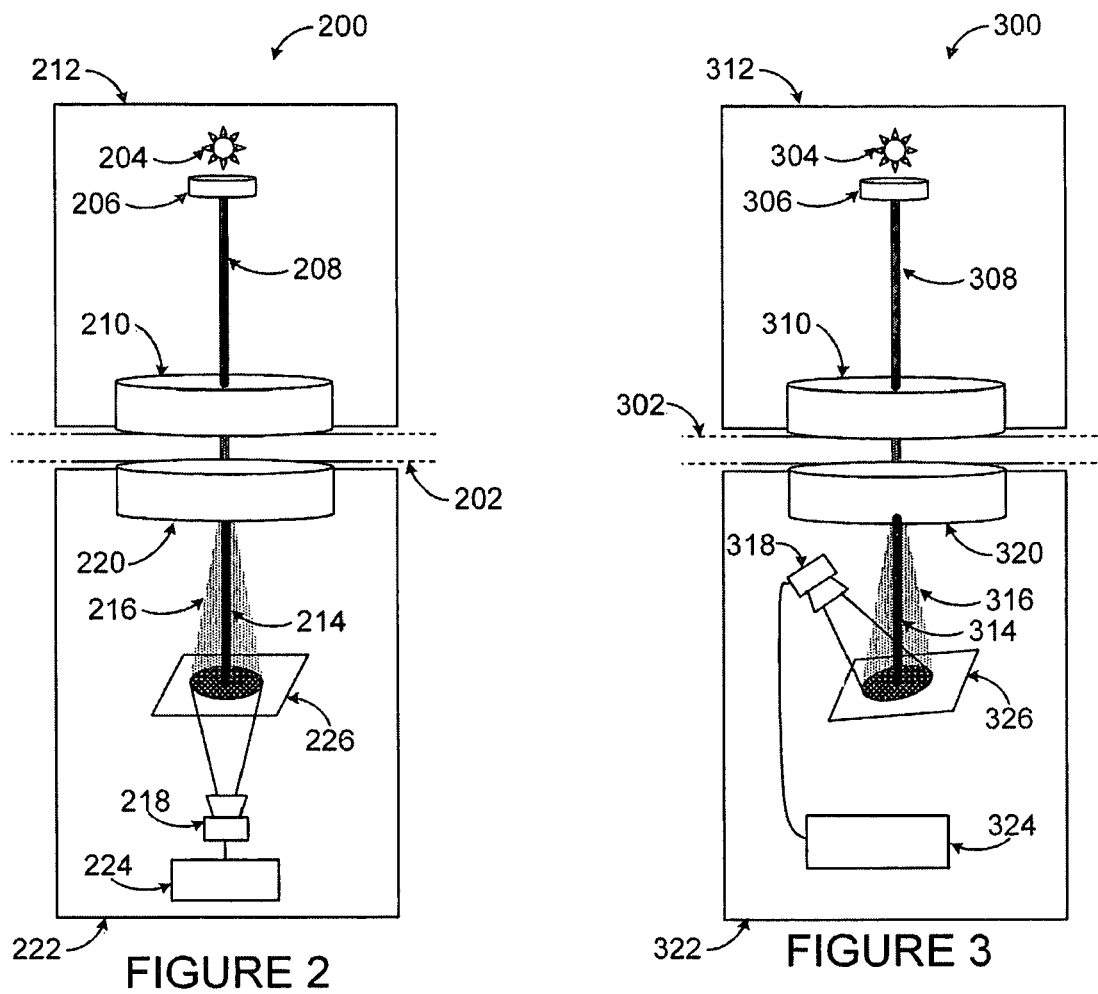
FIGURE 2
FIGURE 3
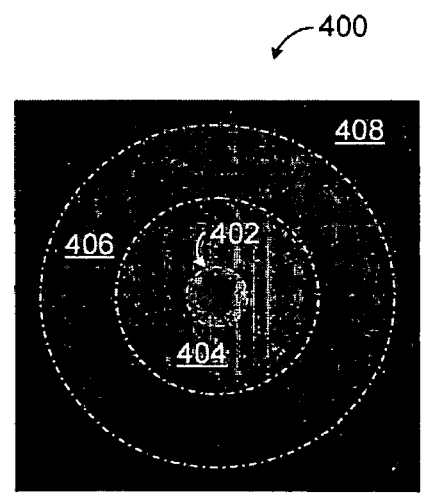
FIGURE 4

APPARATUS AND METHOD FOR MEASURING HAZE OF SHEET MATERIALS OR OTHER MATERIALS

TECHNICAL FIELD

This disclosure relates generally to measurement systems and more specifically to an apparatus and method for measuring haze of sheet materials or other materials.

BACKGROUND

Many transparent, translucent, or other non-opaque materials are produced in long webs or sheets. One characteristic of these types of materials is haze, which refers generally to the scattering of light passing through the materials. Haze typically reduces the contrast of objects viewed through the materials. For example, haze in a plastic sheet used in product packaging might reduce the clarity of lettering viewed through the plastic sheet. Low haze may be important or essential for certain applications, such as consumer electronics packaging or medical device packaging.

Haze measurements typically occur in laboratory settings. For example, a sample of a material can be positioned against an entrance port of an integrating sphere, which can measure the haze of the sample. However, conventional laboratory instruments for measuring haze are typically not suitable for use in a manufacturing or processing environment. Moreover, conventional laboratory instruments for measuring haze are typically contact-type devices, meaning the devices must be placed in physical contact with a material.

SUMMARY

This disclosure provides an apparatus and method for measuring haze of sheet materials or other materials.

In a first embodiment, a method includes illuminating a material with first light and capturing an image of second light transmitted through the material. The method also includes analyzing multiple regions of the image and determining one or more haze measurements associated with the material based on analyzing the multiple regions. The method further includes storing and/or outputting the one or more haze measurements.

In a second embodiment, an apparatus includes at least one memory configured to store an image of light transmitted through a material. The apparatus also includes at least one processor configured to analyze multiple regions of the image and determine one or more haze measurements associated with the material based on analyzing the multiple regions.

In a third embodiment, a system includes an image detector configured to capture an image of light transmitted through a material. The system also includes an analyzer configured to analyze multiple regions of the image and determine one or more haze measurements associated with the material based on analyzing the multiple regions.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIGS. 1 through 3 illustrate example systems for measuring haze of sheet materials or other materials according to this disclosure;

FIG. 4 illustrates an example image used for measuring haze of sheet materials or other materials according to this disclosure;

DETAILED DESCRIPTION

FIGS. 1 through 9, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
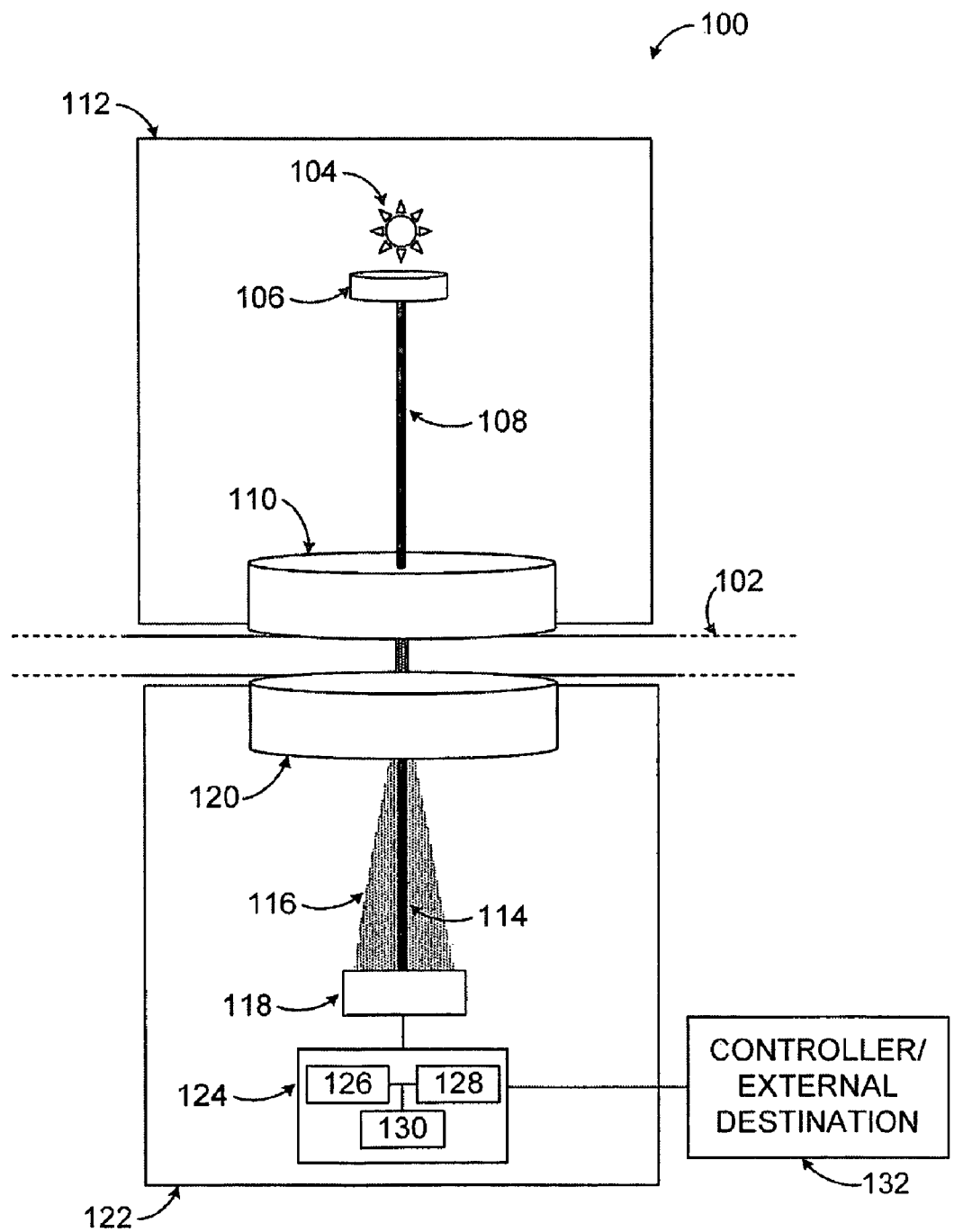

FIGS. 1 through 3 illustrate example systems for measuring haze of sheet materials or other materials according to this disclosure. As shown in FIG. 1, a system 100 is used to measure the haze of a material 102. The material 102 here represents a moving web or sheet of non-opaque material, such as plastic. However, the material 102 could represent any other material(s) in any suitable form(s), such as glass.

In this example, the system 100 includes a light source 104 and optics 106 that are used to produce a collimated beam 108. The light source 104 represents any suitable source of illumination. For example, the light source 104 could include one or more monochrome or narrow-band sources, such as one or more light emitting diodes (LEDs) or lasers. The light source 104 could also include one or more polychrome sources or multiple narrow-band sources, such as multiple LEDs or lasers. The light source 104 could further include spectrally rich sources, such as xenon or other gas-discharge sources, incandescent sources, black body sources, or wide-band LEDs. The light source 104 could optionally include filters or other components for spectral shaping, and the light source 104 could have continuous or pulsed operation.

The optics 106 create the collimated beam 108 using the illumination provided by the light source 104. Any suitable optics 106 could be used, such as masks, lenses, mirrors, or prisms. The collimated beam 108 represents any suitable collimated beam of light. The collimated beam 108 could, for example, represent a beam of light with a circular cross-section having a diameter of at least 1 mm. The collimated beam 108 may have a radially symmetric intensity distribution and a small divergence angle (such as less than 1°). The collimated beam 108 may strike the material 102 at any suitable angle, such as 90°.

A light trap 110 helps to ensure that ambient light is substantially excluded from the measurement location of the material 102. The light trap 110 could represent, for example, a suitable arrangement of baffles or annular light traps that exclude ambient light while providing an unhindered path for the collimated beam 108. A housing 112 can support the components used to produce the collimated beam 108 and can also block ambient light.

Light from the collimated beam 108 strikes the material 102 and is transmitted through the material 102, emerging as transmitted light. The transmitted light includes light 114 traveling along the same general path as the collimated beam 108, meaning this light was not substantially scattered by the material 102. The transmitted light also includes light 116 traveling along a canonical path that diverges away from the path of the collimated beam 108, meaning this light was scattered by the material 102 to a more significant degree. The canonical path could have a subtending angle of at least 10° at its apex, and the canonical path could intersect the material 102 over a larger area than the collimated beam 108. Note that the amount of light 114 and the amount of light 116 vary depending on the haze of the material 102.

The light 114 and 116 strikes an image detector 118, which captures an image of the light 114 and 116. The image detector 118 could, for example, measure the intensity of the light directly incident on each pixel of the detector 118. The image detector 118 could include pixels directly in line with the collimated beam 108 to measure the light 114 and additional pixels to measure the light 116. The image detector 118 may include an imaging area that is large enough to capture most or all of the light 116 within the canonical path.

The image detector 118 includes any suitable image capturing device or devices, such as a charge-coupled device (CCD), a complimentary metal oxide semiconductor (CMOS) device, or a charge injection device (CID). In particular embodiments, the image detector 118 includes a two-dimensional detector array, such as an array of monochrome or RGB detectors. Also, the image detector 118 could have sufficient dynamic range so that pixels are not saturated during image measurements (even if all light from the collimated beam 108 strikes the pixels measuring the light 114). Other components could also be used with the image detector 118, such as an arbitrary spectral filter. Note that the light striking the image detector 118 could be unfocussed, although standard detector micro-optics or other non-focusing optics could be used. Also note that when a pulsed light source 104 is used, the image detector 118 can be synchronized with the light source 104 to capture images at the appropriate times.

A light trap 120 and a housing 122 help to ensure that ambient light is substantially excluded from the measurement location of the material 102. The light trap 120 could exclude ambient light while providing an unhindered path for the light 114 and 116 to the detector 118. The housing 122 could also support the components within the housing.

An analyzer 124 receives images captured by the image detector 118 and analyzes the images to determine one or more haze measurements for the material 102. As described in more detail below, the analyzer 124 could process a captured image by identifying an amount of light striking different regions of the image detector 118. For example, the analyzer 124 could measure the amount of light in a central disc of the image and in one or more concentric regions around the disc. These amounts of light can be used to calculate values such as raw haze, haze blur, and haze fuzz of the material 102. The analyzer 124 includes any hardware, software, firmware, or combination thereof for analyzing images to determine haze measurements. The analyzer 124 could, for example, include one or more processors 126 and one or more memories 128 storing instructions and data used, generated, or collected by the processors 126 (such as images captured by the image detector 118). The analyzer 124 could also include one or more network interfaces 130 facilitating communication over one or more networks, such as an Ethernet interface.

Haze measurements from the analyzer 124 could be used in any suitable manner. For example, the haze measurements could be provided to a controller 132 in a manufacturing system that produces the material 102. The controller 132 could then adjust the production of the material 102 based on the measurements. In this way, the haze measurements provided by the analyzer 124 can be used to adjust pigments or process conditions (like temperature or pressure) used to produce the material 102. This may help to ensure that the haze of the material 102 stays within defined limits. The haze measurements could also be provided to any other suitable destination 132, such as to a database or other memory for storage or to a display for graphical presentation to a user. The haze measurements could be used for any other suitable purpose, such as to inspect the material 102 after manufacture. Note that the analyzer 124 could represent a stand-alone component or could be incorporated into a component or system that uses the haze measurements, such as when the analyzer 124 is implemented within the controller 132.

As shown in FIG. 2, a system 200 is used to measure the haze of a material 202, such as a sheet. The system 200 includes a light source 204 and optics 206 that produce a collimated beam 208. The system 200 also includes a light trap 210 and a housing 212. Light from the collimated beam 208 emerges from the material 202 as light 214 and light 216. The system 200 further includes an image detector 218, a light trap 220, a housing 222, and an analyzer 224. These elements could be the same as or similar to the corresponding elements in FIG. 1. Although not shown, the analyzer 224 could be coupled to a controller or other external destination(s) 132.

In this example, the light 214 and 216 emerging from the material 202 is not provided directly to the image detector 218. Rather, the light 214 and 216 illuminates one side of a target surface 226, and the image detector 218 captures an image of the other side of the target surface 226. The target surface 226 can be optically thin so that the illumination by the light 214 and 216 on one side is minimally blurred or distorted when viewed from the other side. The target surface 226 may represent a flat surface that is generally parallel to the material 202. The target surface 226 could be formed from any suitable material(s), such as one or more high diffuse translucent materials.

As shown in FIG. 3, a system 300 is used to measure the haze of a material 302. The system 300 includes a light source 304 and optics 306 producing a collimated beam 308. The system 300 also includes a light trap 310 and a housing 312. Light from the collimated beam 308 emerges from the material 302 as light 314 and light 316. The system 300 further includes an image detector 318, a light trap 320, a housing 322, and an analyzer 324. These elements could be the same as or similar to the corresponding elements in FIGS. 1 and 2. Also, the analyzer 324 could be coupled to a controller or other external destination(s) 132.

In this example, the light 314 and 316 emerging from the material 302 is not provided directly to the image detector 318. Rather, the light 314 and 316 is reflected off a target surface 326 to the image detector 318. The target surface 326 may represent a generally flat surface that is parallel or at a slight or moderate angle to the material 302. The target surface 326 reflects the light 314 and 316 to the image detector 318, allowing the image detector 318 to be placed in a location that does not obstruct the light 314 and 316. The target surface 326 could be formed from any suitable material(s), such as one or more highly reflective materials.

Although FIGS. 1 through 3 illustrate example systems 100-300 for measuring haze of sheet materials or other materials, various changes may be made to FIGS. 1 through 3. For example, any suitable number of light sources, optics, and collimated beams could be used to illuminate a material. Also, any suitable number of target surfaces, image detectors, and analyzers could be used to measure and analyze light from the material. Further, the arrangements and positions of the components in these figures are for illustration only. In addition, each system could include any other or additional components according to particular needs, such as mirrors, prisms, or other optics for folding a light path as needed.

FIG. 4 illustrates an example image 400 used for measuring haze of sheet materials or other materials according to this disclosure. The image 400 shown in FIG. 4 could, for example, be captured by any of the image detectors in the systems of FIGS. 1 through 3.

In this example, the image 400 can be divided into multiple regions 402-406. The region 402 represents a central disc or other area capturing light that has essentially passed directly through a material being examined. This light has therefore not been substantially scattered due to haze of the material. The regions 404-406 represent annual or other areas around the central region 402. These regions 404-406 capture light that has been scattered to differing degrees due to haze of the material. The image 400 may also include one or more excluded regions 408, where light in the excluded regions 408 is not analyzed.

Note that while the regions 402-406 are shown as being contiguous, there can optionally be annular or other spaces between these regions 402-406. Also note that while the regions 404-406 are shown as being annular, each of these regions could be replaced by a disc or other shape that includes more-inner regions. For example, the region 404 could be replaced by a disc that covers both the regions 402-404 in FIG. 4, and the region 406 could be replaced by a disc that covers all three regions 402-406 in FIG. 4. Further note that the sizes, shapes, and positions of the regions 402-406 may be static or dynamic. For instance, the regions 402-406 can be dynamically centered around the centroid of the image 400, the maximum of the image 400, or the maximum of a smoothed version of the image 400. Also, the diameters of the regions 402-406 could be provided by an external source or calculated based on a radial falloff curve of the pixel values (which can be determined using various heuristics). Other or additional techniques could also be used to define the regions 402-406.

In some embodiments, to process the image 400, an analyzer can add the pixel values in each region 402-406 to produce a sum for that region. Pixels that straddle a boundary between two regions could be handled in various ways. For example, those pixels could be omitted from the analysis. As another example, each pixel could be included in the region where the pixel's center is located. As a third example, a pixel can be fractionally included in both regions based on the percentage of the pixel in each region. As a fourth example, weighting factors can be applied to the pixels in a region before summing them. Weighting factors can be used, for instance, to reduce the effect of pixels that are near the boundaries of a region or that are in more than one region. Weighting factors can also be used to increase the effect of pixels that are not close to a region boundary or that are in only one region.

The sums associated with the regions 402-406 can then be used to calculate one or more haze measurements. For example, raw haze represents the amount of diffused light in at least one non-central region divided by the total amount of light. One example raw haze value can be calculated as:

$$\text{Raw Haze} = \frac{\text{Sum}(R_2) + \text{Sum}(R_3)}{\text{Sum}(R_1) + \text{Sum}(R_2) + \text{Sum}(R_3)} \quad (1)$$

where Sum ($R_1$) represents the sum of pixel values in the region 402, Sum ($R_2$) represents the sum of pixel values in the region 404, and Sum ($R_3$) represents the sum of pixel values in the region 406. Multiple raw haze values could be computed by omitting one of Sum ($R_2$) and Sum ($R_3$) in the numerator of Equation (1) or by using different definitions of the regions 402-406. In particular embodiments, each raw haze value could be converted into a corrected raw haze value using one or more calibration curves, which can be obtained by taking measurements of raw haze using one or more standards of known haze.

Other haze measurements could include haze blur and haze fuzz. Haze blur represents a ratio of slightly diffused light to essentially direct light, which can be expressed as:

$$\text{Haze Blur} = \frac{\text{Sum}(R_2)}{\text{Sum}(R_1)}. \quad (2)$$

Haze fuzz represents a ratio of moderately diffused light to slightly diffused light, which can be expressed as:

$$\text{Haze Fuzz} = \frac{\text{Sum}(R_3)}{\text{Sum}(R_2)}. \quad (3)$$

Any other or additional haze measurements could be used here, such as other measurements based on ratios involving single regions or combinations of regions in the image 400. Calibration curves could also be used to produce corrected haze blur and haze fuzz measurements.

Although FIG. 4 illustrates an example image 400 used for measuring haze of sheet materials or other materials, various changes may be made to FIG. 4. For example, the image 400 could include any suitable number of regions, and those regions could have any suitable size, shape, and position. Also, the image 400 could be analyzed in any other suitable manner.

Figure 5:
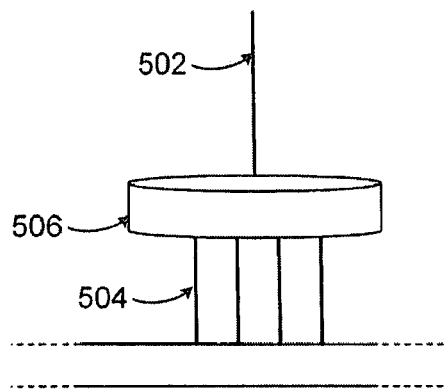
FIGS. 5 through 8 illustrate example variations for measuring haze of sheet materials or other materials according to this disclosure.

FIGS. 5 through 8 illustrate example variations for measuring haze of sheet materials or other materials according to this disclosure. As shown in FIG. 5, a single light beam 502 could be divided into multiple collimated beams 504 using optics 506. The optics 506 could, for example, represent a beam splitter and a collimator. The beam splitter could include diffractive optics, prisms, mirrors, or other components. Each of the collimated beams 504 could be incident on a different area of the material being examined, such as by forming a linear or grid pattern or other spatial pattern. The collimated beams 504 may or may not have the same characteristics, such as diameter or intensity.

Figure 6:
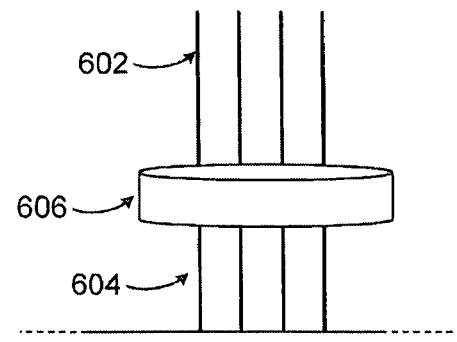

As shown in FIG. 6, multiple light beams 602 could be collimated to produce multiple collimated beams 604 using optics 606. The light beams 602 could include monochrome or polychrome beams. The optics 606 could, for example, represent a collimator and may optionally include a beam splitter. Again, each of the collimated beams 604 could be incident on a different area of the material being examined. Also, the collimated beams 604 may or may not have the same characteristics, such as spectrum or polarization.

Figure 7:
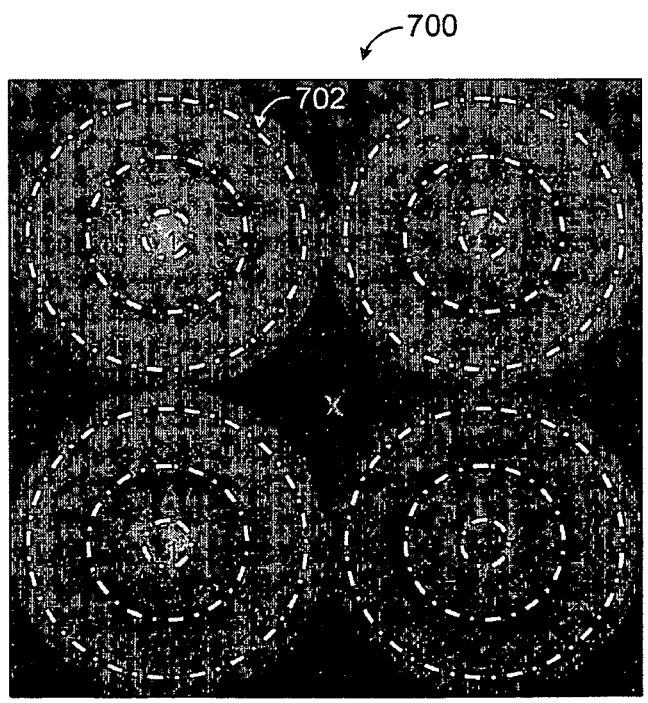

In either case, the analysis of the material may be performed using images of multiple areas of the material (where the multiple light beams 504 or 604 are transmitted through the material). FIG. 7 illustrates an example image 700 used for measuring haze of sheet materials or other materials. Here, the image 700 includes multiple sets 702 of regions. The regions in each set 702 are similar to those shown in FIG. 4, but there are now four sets 702 of those regions. Haze measurements can be determined for each set 702 of regions. Note that each set 702 can be associated with its own beam(s) of light and that one or multiple image detectors could be used to capture images of the sets 702. If a single detector is used, the image 700 can be segmented into different sections (each containing one set 702), where the segmentation can be static or dynamic.

When used with the technique in FIG. 5, the analysis of the image 700 may identify spatial variations of the haze in the material. When used with the technique in FIG. 6, the analysis of the image 700 may identify variations of the haze based on changes in beam properties (such as wavelength or polarization).

Figure 8:
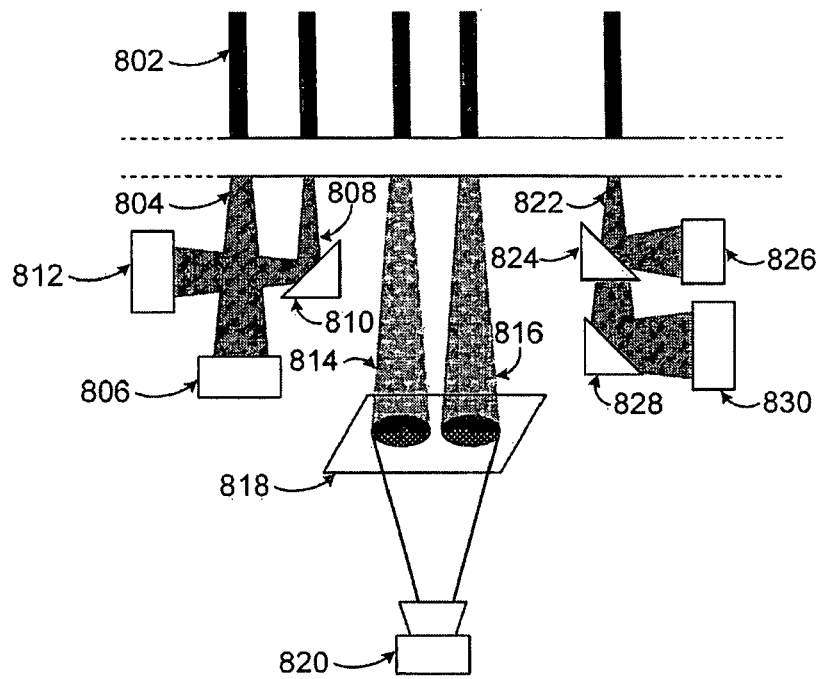

FIG. 8 illustrates another example system 800 for measuring haze of sheet materials or other materials. In this example, a material is illuminated using multiple collimated beams 802. Light 804 associated with a first (monochrome) collimated beam is provided to an unfocussed monochrome image detector 806. Light 808 associated with a second (polychrome) collimated beam is reflected off a mirror 810 and provided to an unfocussed polychrome image detector 812. Light 814-816 associated with third and fourth (monochrome) collimated beams is provided to a translucent target surface 818, and an image detector with focused optics 820 captures an image on the target surface 818. Light 822 associated with a fifth (polychrome) collimated beam is divided by a dichroic mirror 824, which provides part of the light 822 to an unfocussed image detector 826. The other part of the light 822 is reflected off a mirror 828 and provided to another unfocussed image detector 830.

As can be seen in FIGS. 5 through 8, a wide variety of techniques can be used to illuminate a material, direct light to or from the material, and measure light from the material. In general, light transmitted through a material can be detected by one or multiple image detectors and may optionally be split. Splitting using mirrors or prisms can be done so that each of multiple image detectors receives light from a different portion of the material. Splitting using gratings, dichroic mirrors, or filters can be done so that each of multiple image detectors receives light having different spectral characteristics. Each image detector can receive light from one or more illuminated areas of a material (such as the full canonical light from each illuminated area), and the image detectors may or may not be similar. The image detectors could differ in image scale, number of pixels, spectral sensitivity (whether monochrome or polychrome), and focusing optics (or lack thereof). In addition, polychrome light can be imaged in various ways, such as by integrating the light using a monochrome detector (optionally with bandpass or bandstop filters). The polychrome light can also be divided among multiple detectors receiving light in different spectral ranges (via filters or gratings). Spectral filters could be incorporated directly into photosensitive elements of an image detector, such as when a Bayer mask is used on a CCD or CMOS array.

Although FIGS. 5 through 8 illustrate example variations for measuring haze of sheet materials or other materials, various changes may be made to FIGS. 5 through 8. For example, any individual or subset of these variations could be used in any given situation. Also, a wide variety of other variations could also be made.

Figure 9:
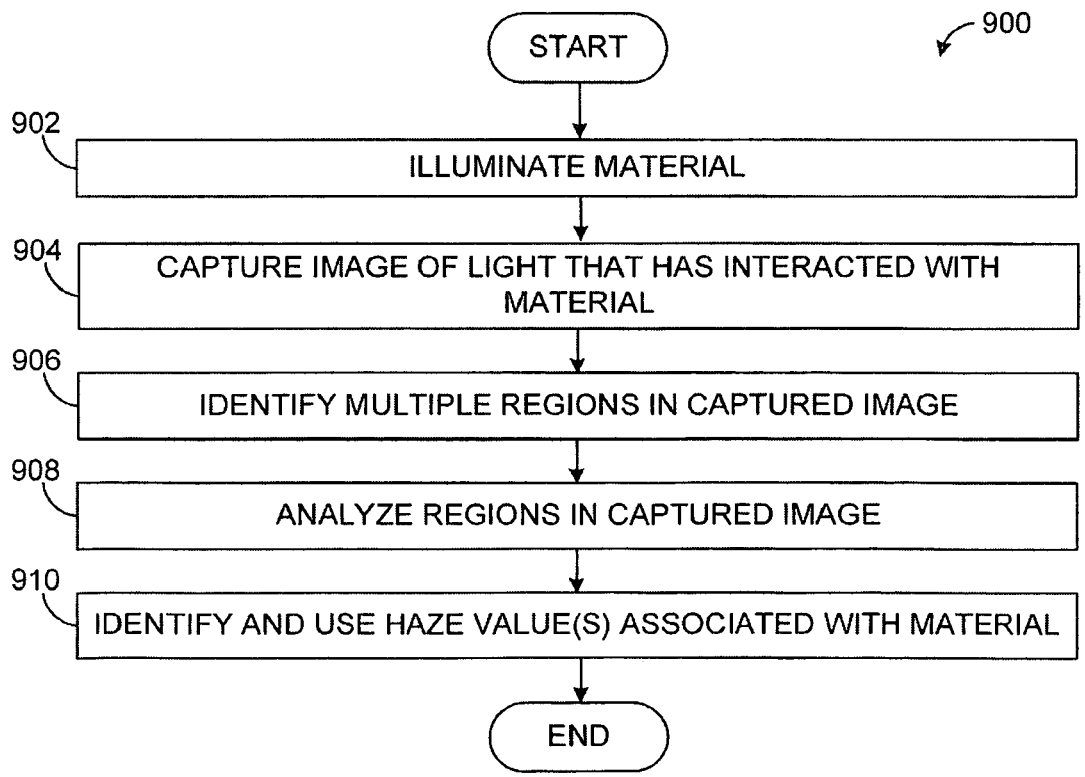
FIG. 9 illustrates an example method for measuring haze of sheet materials or other materials according to this disclosure.

FIG. 9 illustrates an example method 900 for measuring haze of sheet materials or other materials according to this disclosure. As shown in FIG. 9, a material is illuminated at step 902. This could include, for example, illuminating a sheet of material using one or more collimated beams of light. An image of light that has interacted with the material is captured at step 904. This could include, for example, capturing a monochrome or polychrome image of the light that has been transmitted through the sheet of material. The light can be received directly or indirectly from the material.

Multiple regions are identified in the captured image at step 906. This could include, for example, identifying static or dynamic regions in the image. The regions could include a central disc as well as outer annual regions (or larger discs). The regions in the image are analyzed at step 908. This could include, for example, summing the values of the pixels in each region to determine a total sum for that region. Pixels spanning multiple regions could be handled in any suitable manner.

One or more haze values are identified and used at step 910. This could include, for example, using the sums associated with the different regions to calculate raw haze, haze blur, and haze fuzz values. This may also include using one or more calibration curves to adjust the computed haze values. The haze values could then be stored, output to a process controller or other destination, used to modify or control a production process, or used in any other suitable manner.

Although FIG. 9 illustrates an example method 900 for measuring haze of sheet materials or other materials, various changes may be made to FIG. 9. For example, as noted above, a number of variations could be used for illuminating a material, measuring light from the material, and analyzing the results. Also, while shown as a series of steps, various steps in FIG. 9 could overlap, occur in parallel, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   illuminating a material with first light;
   capturing an image of second light transmitted through the material;
   analyzing multiple regions of the image;

determining one or more haze measurements associated with the material based on analyzing the multiple regions; and at least one of storing and outputting the one or more haze measurements;

wherein the multiple regions of the image comprise:
   a first region; and
   a second region comprising either (i) a region around the first region or (ii) a region larger than and including the first region.

2. The method of claim 1, wherein analyzing the multiple regions of the image comprises:
   summing pixel values in each region of the image to produce a total pixel value for that region.

3. The method of claim 2, wherein summing the pixel values in each region comprises applying weighting factors to the pixel values and summing the weighted pixel values.

4. The method of claim 2, wherein each pixel straddling a boundary between two regions of the image are fractionally included in both of those regions.

5. The method of claim 1, wherein:
   the first region comprises a first disc;
   the second region comprises either (i) a first annular region around the first region or (ii) a second disc larger than and including the first disc; and
   the multiple regions further comprise a third region, the third region comprising either (i) a second annular region around the second region or (ii) a third disc larger than and including the first and second discs.

6. The method of claim 1, further comprising:
   dynamically defining the multiple regions in the image based on pixel values in the image.

7. The method of claim 1, wherein determining the one or more haze measurements comprises determining at least one of: a raw haze of the material, a haze blur of the material, and a haze fuzz of the material.

8. The method of claim 1, wherein:
   the first light comprises multiple beams of light; and
   the image of the second light comprises at least one of:
      a single image having multiple areas associated with different ones of the beams of light; and
      multiple images associated with different ones of the beams of light.

9. The method of claim 1, wherein:
   the first light comprises multiple beams of light having at least one differing characteristic; and
   determining the one or more haze measurements comprises determining one or more haze measurements for each of the beams.

10. The method of claim 1, further comprising:
   adjusting operation of a system producing the material based on the one or more haze measurements.

11. An apparatus comprising:
   at least one memory configured to store an image of light transmitted through a material; and
   at least one processor configured to analyze multiple regions of the image and determine one or more haze measurements associated with the material based on analyzing the multiple regions;
   wherein the multiple regions of the image comprise:
      a first region; and
      a second region comprising either (i) a region surrounding the first region or (ii) a region larger than and including the first region.

12. The apparatus of claim 11, wherein the at least one processor is configured to analyze the multiple regions of the image by summing pixel values in each region of the image to produce a total pixel value for that region.

13. The apparatus of claim 11, wherein:
   the first region comprises a first disc;
   the second region comprises either (i) a first annular region around the first region or (ii) a second disc larger than and including the first disc; and
   the multiple regions further comprise a third region, the third region comprising either (i) a second annular region around the second region or (ii) a third disc larger than and including the first and second discs.

14. The apparatus of claim 11, wherein the at least one processor is further configured to dynamically define the multiple regions in the image based on pixel values in the image.

15. The apparatus of claim 11, wherein:
   the image comprises a single image having multiple areas associated with different beams of light transmitted through the material; and
   wherein the at least one processor is further configured to dynamically segment the image into the multiple areas.

16. The apparatus of claim 11, wherein the at least one processor is further configured to adjust operation of a system producing the material based on the one or more haze measurements.

17. The apparatus of claim 11, wherein the material comprises a web or sheet.

18. A system comprising:
   an image detector configured to capture an image of light transmitted through a material; and
   an analyzer configured to analyze multiple regions of the image and determine one or more haze measurements associated with the material based on analyzing the multiple regions;
   wherein the multiple regions of the image comprise:
      a first region; and
      a second region comprising either (i) a region surrounding the first region or (ii) a region larger than and including the first region.

19. The system of claim 18, further comprising:
   a controller configured to adjust operation of a system producing the material based on the one or more haze measurements.

20. The system of claim 18, wherein the analyzer is configured to analyze the multiple regions of the image by summing pixel values in each region of the image to produce a total pixel value for that region.

21. The system of claim 18, wherein:
   the first region comprises a first disc;
   the second region comprises either (i) a first annular region around the first region or (ii) a second disc larger than and including the first disc; and
   the multiple regions further comprise a third region, the third region comprising either (i) a second annular region around the second region or (ii) a third disc larger than and including the first and second discs.

* * * * *